US009433216B2

(12) United States Patent
Watanabe et al.

(10) Patent No.: US 9,433,216 B2
(45) Date of Patent: Sep. 6, 2016

(54) CONSTRUCTION MATERIAL PRESERVATIVE

(75) Inventors: Shinya Watanabe, Makinohara (JP); Satoru Makita, Odawara (JP); Motoaki Yabe, Odawara (JP); Shigebumi Arai, Odawara (JP)

(73) Assignee: Nippon Soda Co., Ltd., Tokyo (JP)

(*) Notice: Subject to any disclaimer, the term of this patent is extended or adjusted under 35 U.S.C. 154(b) by 0 days.

(21) Appl. No.: 13/261,775

(22) PCT Filed: May 9, 2012

(86) PCT No.: PCT/JP2012/061866
§ 371 (c)(1),
(2), (4) Date: Nov. 7, 2013

(87) PCT Pub. No.: WO2012/153760
PCT Pub. Date: Nov. 15, 2012

(65) Prior Publication Data
US 2014/0066418 A1    Mar. 6, 2014

(30) Foreign Application Priority Data

May 11, 2011   (JP) ................. 2011-106609
May 11, 2011   (JP) ................. 2011-106610

(51) Int. Cl.
| A01N 25/34 | (2006.01) |
| A61K 9/00 | (2006.01) |
| A01N 55/02 | (2006.01) |
| A01N 59/16 | (2006.01) |

(52) U.S. Cl.
CPC .............. *A01N 55/02* (2013.01); *A01N 59/16* (2013.01)

(58) Field of Classification Search
CPC .................................................. A01N 59/16
See application file for complete search history.

(56) References Cited

U.S. PATENT DOCUMENTS

| 2,596,631 | A |  | 5/1952 | Whitacre et al. |
| 6,541,038 | B1 | * | 4/2003 | Tanaka et al. ................ 424/618 |
| 7,335,248 | B2 | * | 2/2008 | Abou-Nemeh ............ 106/18.34 |
| 2005/0239763 | A1 | * | 10/2005 | Motyka et al. ............... 514/184 |
| 2007/0213426 | A1 | * | 9/2007 | Abou-Nemeh ............... 523/122 |
| 2007/0227399 | A1 |  | 10/2007 | Abou-Nemeh |
| 2010/0136074 | A1 | * | 6/2010 | Bukshpan et al. ............ 424/404 |
| 2010/0297259 | A1 | * | 11/2010 | Wilson et al. ................ 424/635 |

FOREIGN PATENT DOCUMENTS

| DE | 202006013769 U1 | 1/2007 |
| EP | 0 651 945 A1 | 5/1995 |
| JP | 07-068508 A | 3/1995 |
| JP | 10-272610 A | 10/1998 |
| JP | 11-060411 A | 3/1999 |
| JP | 11-165303 A | 6/1999 |
| JP | 11-189504 A | 7/1999 |
| JP | 2000-256365 A | 9/2000 |
| JP | 2002-205906 A | 7/2002 |
| JP | 2002-294890 A | 10/2002 |
| JP | 2005-145923 A | 6/2005 |
| JP | 2005-298418 A | 10/2005 |
| JP | 2006-219463 A | 8/2006 |
| JP | 2007-176985 A | 7/2007 |
| JP | 2009-298776 A | 12/2009 |
| JP | 2011-178731 A | 9/2011 |
| WO | WO 93/25080 A1 | 12/1993 |
| WO | WO 2005/084442 A1 | 9/2005 |
| WO | WO 2009/098850 A1 | 8/2009 |
| WO | WO 2009098850 A1 * | 8/2009 |

OTHER PUBLICATIONS

Bonmatin et al. Environmental fate and exposure; neonicotinoids and fipronil. Environ Sci Pollut Res (2015) 22:35-67.*
Yabe, Shigeaki, "Amino Acid Gin Sakutai o Mochiita Kogyo-yo Kokin Bofuzai no Kaihatsu," The Society for Antibacterial and Antifungal Agents, Japan Nenji Taikai Yoshishu, 2009, 36:191.
Yabe, Shigeaki,"Yuki Muki Hybrid-gata Shinki Bofuzai," The Industrial Coating, 2010, 227:49-53.
Office Action dated Jul. 17, 2014, in CN 201280022100.3, with English translation.
Zhijian et al., "Physicochemical Behaviors of Silver in Hydrothermal Solution Containing Amino Acids," Geoscience, Sep. 30, 1996, 10(3):414-421, with English abstract on first page.
Office Action dated Sep. 16, 2014, in JP 2013-514028, with English translation.
Search Report dated Sep. 23, 2014, in EP 12781663.5.
Dorau et al., "An Investigation into the Potential of Ionic Silver as a Wood Preservative," Proceedings from the Woodframe Housing Durability and Disasters Issues Conference, Oct. 4, 2004, Las Vegas, Nevada, 133-145.
Kasuga et al., "Syntheses, Structures, and Antimicrobial Activities of Remarkably Light-Stable and Water-Soluble Silver Complexes with Amino Acid Derivatives, Silver(I) N-Acetylmethioninates," Inorganic Chemistry, Feb. 6, 2012, 51(3):1640-1647.
Kazachenko et al., "Synthesis and Antimicrobial Activity of Silver Complexes with Histidine and Tryptophan," Pharmaceutical Chemistry Journal, May 1, 2000, 34(5):257-258.
McAuliffe et al., "Metal Complexes of the Amino Acid DL-Methionine," Inorganic Chemistry, Nov. 1966, 5(11):1996-2003.
Office Action dated Jul. 17, 2014, in CN 20128002210.3, with English translation.
Zhijian et al., "Physcochemical Behaviors of Silver in Hydrothermal Solution Containing Amino Acids," Geoscience, Sep. 30, 1996, 10(3):414-421, with English abstract on first page.
Office Action dated Jun. 18, 2014, in AU 2012254464.
Wikipedia "wood preservative" retrieved from internet Jun. 16, 2014, http://web.archive.org/web/20100303105011/http://en.wikipedia.org/wiki/Wood_preservation, published on Mar. 3, 2010 as per wayback machine.

* cited by examiner

*Primary Examiner* — Robert A Wax
*Assistant Examiner* — Olga V Tcherkasskaya
(74) *Attorney, Agent, or Firm* — Foley & Lardner LLP

(57) ABSTRACT

The present invention provides a construction material preservative for wood and the like that retains preservative effects over a long period of time and continuously demonstrates those effects even at low concentrations even when using in combination with an insecticide. The construction material preservative contains a water-soluble silver-amino acid complex composed of 1 molar part of silver and 1 to 3 molar parts of amino acid.

8 Claims, No Drawings

CONSTRUCTION MATERIAL PRESERVATIVE

TECHNICAL FIELD

The present invention relates to a novel construction material preservative.

The present invention claims priority on the basis of Japanese Patent Application No. 2011-106609 filed in Japan on May 11, 2011 and Japanese Patent Application No. 2011-106610 filed in Japan on May 11, 2011, the contents of which are incorporated herein by reference.

BACKGROUND OF THE INVENTION

Known examples of construction material preservatives containing silver, and particularly those used as wood preservatives, include a wood preservative mainly composed of a silver complex salt of chitosan (Patent Document 1), a wood preservative composed of a suspension of zeolite having a particle diameter of 500 microns or less loaded with silver ions (Patent Document 2), a wood preservative composed of a carboxyalkylthiosuccinic acid and a metal compound such as a silver compound (Patent Document 3), a wood preservative containing a metal salt such as a silver salt, a phenolic compound, a thiosulfate or thiocyanate, and an amine that forms a complex with a metal ion (Patent Document 4), and a wood preservative that contains a silver-maleic anhydride salt and monoethanolamine (Patent Document 5).

On the other hand, a silver-histidine complex is known as an example of a silver-amino acid complex that can be used as a bactericidal agent or antibacterial agent (Patent Document 6). In addition, insecticide components such as neonicotinoid-based compounds are known that have control effects against termites (Patent Documents 7 to 9).

DOCUMENTS OF RELATED ART

Patent Documents

Patent Document 1: Japanese Unexamined Patent Application, First Publication No. H07-68508
Patent Document 2: Japanese Unexamined Patent Application, First Publication No. H10-272610
Patent Document 3: Japanese Unexamined Patent Application, First Publication No. H11-60411
Patent Document 4: Japanese Unexamined Patent Application, First Publication No. H11-165303
Patent Document 5: Japanese Unexamined Patent Application, First Publication No. H11-189504
Patent Document 6: Japanese Unexamined Patent Application, First Publication No. 2000-256365
Patent Document 7: International Publication No. WO 93/25080
Patent Document 8: Japanese Unexamined Patent Application, First Publication No. 2002-294890
Patent Document 9: Japanese Unexamined Patent Application, First Publication No. 2006-219463

DISCLOSURE OF THE INVENTION

Problems to be Solved by the Invention

However, the efficacy of wood and other construction material preservatives containing silver known in the prior art has not necessarily been adequate, and there have also been problems with stability.

In addition, although insecticide components such as neonicotinoid-based compounds are known to demonstrate efficacy against termites as previously described, they have the problem of being required to be used at comparatively high concentrations in order to obtain adequate efficacy.

On the other hand, although silver-amino acid complexes such as silver-histidine complexes are known to demonstrate efficacy as antibacterial agents or bactericidal agents as previously described, they are not known to demonstrate efficacy against wood decaying fungi, and therefore are not known to be used as a preservative of construction materials such as wood.

In addition, although Patent Document 1 describes that a copper or zinc complex of chitosan has anti-termite effects, silver-amino acid complexes are not known to have anti-termite effects.

An object of the present invention is to provide a construction material preservative for wood and the like that continuously demonstrates preservative effects for a long period of time and has insecticidal action and effects even at low concentrations.

Means to Solve the Problems

The present invention includes the following:
(1) a construction material preservative containing a water-soluble silver-amino acid complex;
(2) the construction material preservative described in (1), wherein the water-soluble silver-amino acid complex is composed of 1 molar part of silver and 1 to 3 molar parts of amino acid;
(3) the construction material preservative described in (1) or (2), wherein the amino acid is at least one type selected from the group consisting of histidine, methionine and N-acetylmethionine;
(4) the construction material preservative described in any of (1) to (3), further containing water;
(5) the construction material preservative described in any of (1) to (4), further containing an insecticide component;
(6) the construction material preservative described in (5), wherein 0.1 parts by weight to 40 parts by weight of the insecticide component is contained relative to 1 part by weight of the water-soluble silver-amino acid complex;
(7) the construction material preservative described in (5) or (6), wherein 0.0001% by weight to 0.5% by weight of the water-soluble silver-amino acid complex, 0.0001% by weight to 0.5% by weight of the insecticide component, and 10% by weight or more of water are contained;
(8) the construction material preservative described in any of (5) to (7), wherein the insecticide component has a saturated solubility in water at 25° C. of 500 ppm or more;
(9) the construction material preservative described in any of (5) to (8), wherein the insecticide component is a neonicotinoid-based compound;
(10) the construction material preservative described in any of (5) to (9), wherein the insecticide component is at least one type selected from the group consisting of nitenpyram, imidacloprid, acetamiprid, thiamethoxam, clothianidin, dinotefuran and thiacloprid;
(11) the construction material preservative described in any of (1) to (10), which is used to control termites;
(12) the construction material preservative described in any of (1) to (11), wherein the construction material is a foamed resin insulating material or wood;
(13) a construction material processing method, comprising treating a construction material with the construction material preservative described in any of (1) to (12);

(14) the construction material processing method described in (13), wherein the treatment is at least one type selected from the group consisting of coating treatment, immersion treatment, injection treatment, and pressurized injection treatment;

(15) a processed construction material obtained by the construction material processing method described in (13) or (14);

(16) the processed construction material described in (15), wherein the processed construction material is a foamed resin insulating material or wood;

(17) a composition containing a water-soluble silver-amino acid complex and an insecticide component;

(18) the composition described in (17), further containing water;

(19) a composition containing 0.0001% by weight to 0.5% by weight of a water-soluble silver-amino acid complex, 0.0001% by weight to 0.5% by weight of an insecticide component, and 10% by weight or more of water;

(20) the composition described in any of (17) to (19), wherein the insecticide component has a saturated solubility in water at 25° C. of 500 ppm or more;

(21) the composition described in any of (17) to (20), wherein the insecticide component is a neonicotinoid-based compound;

(22) the composition described in any of (17) to (21), wherein the insecticide component is at least one type selected from the group consisting of nitenpyram, imidacloprid, acetamiprid, thiamethoxam, clothianidin, dinotefuran and thiacloprid; and,

(23) the composition described in any of (17) to (22), wherein the amino acid is at least one type selected from the group consisting of histidine, methionine, and N-acetylmethionine.

Effects of the Invention

The construction material preservative of the present invention is extremely safe and demonstrates control effects against a wide spectrum of harmful microorganisms, including wood decaying fungi for which there are few effective chemical agents. Moreover, since the construction material preservative of the present invention also demonstrates insecticidal effects against termites and other wood pests, it demonstrates adequate wood preservative effects without having to use in combination with other types of bactericidal agents, antibacterial agents, fungicides, insecticides or pest repellents and the like.

The construction material preservative of the present invention has low toxicity with respect to acute oral toxicity, skin irritation or mucosal membrane irritation, and does not affect the quality of wood. Moreover, it is able to continuously demonstrate antibacterial, bactericidal, fungicidal and insecticidal effects over a long period of time. Thus, the quality of wood products treated with the construction material preservative of the present invention is not impaired over a long period of time.

In addition, in the case of combining with an insecticide component, adequate efficacy is able to be demonstrated even at a low concentration of the insecticide component due to the synergistic effects thereof.

EMBODIMENTS OF THE INVENTION

The inventors of the present invention found that, when a silver-amino acid complex such as a water-soluble silver-histidine complex is applied to wood, microorganisms such as wood decaying fungi are effectively exterminated, preservative effects are retained for a long period of time, insecticidal effects are demonstrated against wood pests such as termites, and in the case of combining with an insecticide, synergistic effects are demonstrated that allow insecticidal effects to be demonstrated even at low concentrations, thereby leading to completion of the present invention.

The construction material preservative for wood and the like (to simply be referred to as the construction material preservative) of the present invention is a composition that contains a water-soluble silver-amino acid complex. Here, water soluble refers to having solubility in water at 25° C. of preferably 0.1% by weight or more and more preferably 1% by weight or more.

The water-soluble silver-amino acid complex used in the construction material preservative of the present invention is preferably composed of 1 molar part of silver and 1 to 3 molar parts of amino acid, and more preferably composed of 1 molar part of silver and 1.1 to 2.5 molar parts of amino acid.

The concentration of silver in the construction material preservative of the present invention is preferably 0.0002% by weight to 10% by weight, more preferably 0.003% by weight to 5% by weight, and even more preferably 0.2% by weight to 2.5% by weight. In the case the silver concentration is equal to or greater than the aforementioned lower limit value, particularly superior harmful organism control effects are demonstrated. On the other hand, the silver concentration is preferably equal to or less than the aforementioned upper limit value from the viewpoint of production costs.

The water-soluble silver-amino acid complex is prepared by using a silver compound and an amino acid compound.

Although there are no particular limitations on the silver compound used to prepare the water-soluble silver-amino acid complex, a silver compound having an oxidation number of 1 is particularly preferable. Examples of silver compounds include silver nitrate, silver oxide and silver chloride. One type of the silver compound can be used alone or two or more types can be used in combination.

There are no particular limitations on the amino acid compound used to prepare the water-soluble silver-amino acid complex provided the resulting silver-amino acid complex is water-soluble. Examples of amino acid compounds include amino acids and amino acid derivatives.

Examples of amino acids include glycine, alanine, leucine, valine, glutamine, glutamic acid, asparagine, aspartic acid, histidine, lysine, arginine, cysteine, methionine, tyrosine and tryptophan.

Examples of amino acid derivatives include: amino acid salts, such as amino acid hydrochlorides, amino acid sulfates, amino acid ammonium salts, amino acid sodium salts, or amino acid potassium salts; N-acylated amino acids, such as N-formyl amino acid, N-acetyl amino acids, N-propionyl amino acids, or N-butyryl amino acids; N-alkyl amino acids, such as N-methyl amino acids, N-ethyl amino acids, N-n-propyl amino acids, N-isopropyl amino acids, or N-n-butyl amino acids; amino acid amides, such as compounds in which amide nitrogen atoms are not substituted, or compounds in which amide nitrogen atoms are substituted with alkyl groups such as a methyl group, ethyl group, n-propyl group, isopropyl group, or n-butyl group; and amino acid esters, such as amino acid methyl esters, amino acid ethyl esters, amino acid n-propyl esters, amino acid isopropyl esters, or amino acid n-butyl esters.

One type of these amino acid compounds may be used alone or at least two types thereof may be used in combination. Among these, basic amino acids; sulfur-containing amino acids; N-acylated amino acids having a lower acyl group such as a formyl group, acetyl group, or propionyl group; and salts thereof are preferable, basic amino acids, sulfur-containing amino acids, and N-acylated amino acids are more preferable, and basic amino acids and sulfur-containing amino acids are particularly preferable. Histidine, lysine and arginine are preferable as basic amino acids, and histidine is particularly preferable. Methionine is preferable as a sulfur-containing amino acid. N-acetylmethionine is preferable as an N-acylated amino acid.

Although there are no particular limitations on the combination of silver compound and amino acid compound used to prepare the water-soluble silver-amino acid complex, from the viewpoint of storage stability of the resulting water-soluble silver-amino acid complex, the combination of silver oxide and histidine or the combination of silver oxide and methionine is preferable.

Although there are no particular limitations on the method used to prepare the water-soluble silver-amino acid complex, the water-soluble silver-amino acid complex can be prepared by, for example, dissolving a water-soluble silver compound such as silver nitrate in water, and adding and mixing an amino acid compound therewith either directly or after dissolving in water. In addition, the water-soluble silver-amino acid complex can also be prepared by preliminarily dissolving an amino acid compound in water and adding a poorly water-soluble silver compound such as silver oxide or silver chloride thereto followed by stirring.

In preparing the water-soluble silver-amino acid complex, normally 1 to 3 molar parts and preferably 1.1 to 2.5 molar parts of the amino acid compound may be used relative to 1 molar part of silver in the silver compound. If the amount of the amino acid compound is 1 molar part or more, silver ions can be made to be present in the form of a more stable solution, and degeneration such as discoloration, precipitation or settling can be prevented. On the other hand, the amount of the amino acid compound is preferably 3 molar parts or less from the viewpoint of production costs.

The construction material preservative of the present invention may be obtained directly in the form of an aqueous solution by preparing the water-soluble silver-amino acid complex in water as previously described, or it may be obtained in the form of a dry solid of the water-soluble silver-amino acid complex prepared as previously described or a wettable powder or water-soluble powder that contains the water-soluble silver-amino acid complex to be subsequently described.

The concentration of the water-soluble silver-amino acid complex contained in the construction material preservative of the present invention is preferably 0.0005% by weight to 20% by weight, more preferably 0.05% by weight to 10% by weight, and more preferably 0.25% by weight to 5% by weight.

Although there are no particular limitations on the water used in the construction material preservative of the present invention, examples thereof include tap water, purified water, ion exchange water and distilled water. Among these, purified water or ion exchange water is preferable from the viewpoints of stability and economy. Although there are no particular limitations on the proportion of water in the construction material preservative of the present invention, it is preferably selected so that the concentration of the water-soluble silver-amino acid complex is within the aforementioned ranges.

Although there are no particular limitations on the temperature in each step of the production of the construction material preservative of the present invention, it is preferably 10° C. to 30° C. In addition, a known stirring device can be used to mix each component. Contaminants are preferably removed by filtration and the like from the construction material preservative of the present invention produced according to a method like that previously described.

Although there are no particular limitations on the pH of the construction material preservative of the present invention, it is preferably 5 or higher and more preferably 6.5 or higher. Although there are no particular limitations on the upper limit of pH, it is preferably 12 and more preferably 11.

Adjustment of the pH of the construction material preservative may be carried out after having formed the water-soluble silver-amino acid complex, before forming the water-soluble silver-amino acid complex, or during formation of the water-soluble silver-amino acid complex.

A commonly used, known pH adjuster may be used to adjust pH. Examples of pH adjusters include sulfuric acid, nitric acid, citric acid, acetic acid, sodium hydroxide, potassium hydroxide, ammonia and phosphates. Among these, alkaline compounds are preferable. Although there are no particular limitations on these alkaline compounds, sodium hydroxide or potassium hydroxide is preferable.

An insecticide component may be further contained in the construction material preservative of the present invention, and although there are no particular limitations thereon provided the insecticide component has insecticidal effects, it is preferably a compound that dissolves in water, and more preferably that having a saturated solubility in water at 25° C. of 500 ppm or more.

Examples of insecticide components include: neonicotinoid-based compounds, such as nitenpyram, imidacloprid, acetamiprid, thiamethoxam, clothianidin, dinotefuran, and thiacloprid; organic phosphorous-based compounds, such as fenitrothion, phoxim, azinphos-methyl, DDVP, cyanophos, fenthion, diazinon, chlorpyrifos, or phenthoate; carbamate-based compounds, such as aldicarb, methomyl, thiodicarb, carbofuran, carbosulfan, benfuracarb, propoxur, BPMC, carbaryl, pirimicarb, ethiofencarb or fenoxycarb; pyrethroid-based compounds, such as phenothrin, cyphenothrin, permethrin, cypermethrin, fenvalerate, ethofenprox, tralomethrin, deltamethrin, fluvalinate, or cyfluthrin; benzoylurea-based compounds, such as diflubenzuron, chlorfluazuron, hexaflumuron, triflumuron, flufenoxuron, pyriproxyfen, methoprene, or diafenthiuron; pyrazole-based compounds, such as fipronil; nereistoxin-based compounds, such as cartap, or bensultap; macrolide-based compounds, such as abamectin, milbemectin, or spinosad; and boron-based compounds, such as boric acid, or borates.

One type of these insecticide components may be used alone or at least two types thereof may be used in combination.

Among these, boron-based compounds, neonicotinoid-based compounds, pyrethroid-based compounds, carbamate-based compounds, and organic phosphorous-based compounds are preferable from the viewpoint of having potent control effects against termites, and neonicotinoid-based compounds are more preferable from the viewpoints of high degrees of safety and sustained action.

In addition, among neonicotinoid-based compounds, nitenpyram, imidacloprid, acetamiprid, thiamethoxam, clothianidin, dinotefuran, and thiacloprid are preferable, and acetamiprid is particularly preferable.

The construction material preservative of the present invention that contains an insecticide component preferably contains water. As a result of containing water, generation of odor is prevented and the resulting preservative has a higher degree of safety. In addition, sustained control effects against termites are higher and the preservative can be used over a long period of time.

Although examples of water used include tap water, purified water, ion exchange water and distilled water, purified water or ion exchange water is preferable from the viewpoints of stability and economy.

There are no particular limitations on the composite ratios of the water-soluble silver-amino acid complex, insecticide component and water, and although these composite ratios can be arbitrarily selected corresponding to the application, application method, efficacy of each component, physical properties and the like, the insecticide component is preferably used within the range of 0.1 parts by weight to 40 parts by weight relative to 1 part by weight of the water-soluble silver-amino acid complex.

A preferable construction material preservative of the present invention that further contains an insecticide component contains 0.0001% by weight to 0.5% by weight of the water-soluble silver-amino acid complex, 0.0001% by weight to 0.5% by weight of the insecticide component, and 10% by weight or more of water (10% by weight to less than 99.9998% by weight and more preferably 10% by weight to less than 99% by weight), and is preferably used in the form of an aqueous solution.

Other components may also be further contained in the construction material preservative of the present invention. Examples of other components include surfactants, thickeners, antioxidants, photostabilizers, fragrances, antifoaming agents and organic solvents.

Examples of surfactants include: cationic surfactants, such as alkyl trimethyl ammonium salts, dialkyl dimethyl ammonium salts, alkyl benzyl dimethyl ammonium salts, alkyl pyridinium salts, or polyhexamethylene biguanide; anionic surfactants, such as alkylbenzene sulfonates, alkyl sulfates, alkylnaphthalene sulfonates, dialkyl sulfosuccinates, polyoxyethylene alkyl ether sulfates, polyoxyethylene alkyl ether carbonates, ammonium polyoxyethylene styrenated phenyl ether sulfates, lignin sulfonate, higher fatty acid salts, α-olefin fatty acid salts, or α-sulfo fatty acid salts; and amphoteric surfactants, such as alkyl methyl amine oxides, alkyl carboxybetaines or alkyl sulfobetaines.

Examples of thickeners include carboxymethyl cellulose and xanthan gum.

Examples of antioxidants include 2,6-di-t-butyl-4-methylphenol, 2,2'-methylenebis[4-methyl-6-t-butylphenol], and alkyl diphenyl amines.

Examples of photostabilizers include bis(2,2,6,6-tetramethyl-4-sebacate), and hydroxycarboxylic acids, polycarboxylic acids, and salts thereof, disclosed in International Publication No. WO 2009/098850. Among these, glucuronic acid, citric acid, and salts thereof are preferable from the viewpoint of suppressing discoloration of the silver-amino acid complex caused by exposure to light.

Organic solvent may be contained in the construction material preservative of the present invention to a degree that does not impair the object and advantages of the present invention such as safety. Examples of organic solvents include: lower alcohols, such as ethanol or isopropanol; glycol-based solvents, such as ethylene glycol, propylene glycol, dipropylene glycol, polypropylene glycol, or glycerin; ketone-based solvents, such as acetone, methyl ethyl ketone, or propylene carbonate; and polar solvents, such as dimethylformamide, dimethylsulfoxide, acetonitrile, or N-methylpyrrolidone.

In addition, known active ingredients such as fungicides, preservatives, or algaecides, may also be contained in the construction material preservative of the present invention corresponding to the object and application thereof.

Examples of active ingredients include: quaternary ammonium salt-based compounds, such as didecyl dimethyl ammonium chloride (DDAC), or didecyl dimethyl ammonium adipate (DDAA); biguanide-based compounds, such as polyhexamethylene biguanide (PHMB), or chlorhexidine gluconate; pyridinium-based compounds, such as cetyl pyridinium chloride, or dodecyl pyridinium chloride; isothiazoline-based compounds, such as 1,2-benzisothiazolin-3-one, 5-chloro-2-methyl-4-isothiazolin-3-one, 2-methyl-4-isothiazolin-3-one, 2-n-octyl-4-isothiazolin-3-one or N-n-butyl-1, 2-benzisothiazolin-3-one; organic iodine-based compounds, such as 3-iodo-2-propinyl butylcarbamate, pyridine-based compounds, such as 2,3,5,6-tetrachloro-4-(methylsulfonyl) pyridine; pyrithione-based compounds, such as zinc pyrithione, or sodium pyrithione; benzothiazole-based compounds, such as 2-(4-thiocyanomethylthio)benzothiazole; imidazole-based compounds, such as methyl-2-benzimidazole carbamate, or 2-(4-thiazolyl)-benzimidazole; thiocarbamate-based compounds, such as tetramethylthiuram disulfide; nitrile-based compounds such as 2,4,5,6-tetrachloroisophthalonitrile; haloalkylthio-based compounds such as N-(fluorodichloromethylthio)-phthalimide, or N-(fluorodichloromethylthio)-N,N'-dimethyl-N-phenyl-sulfamide; triazole-based compounds, such as α-t-butyl-α(p-chlorophenylethyl)-1H-1,2,4-triazole-1-ethanol (common name: tebuconazole); phenylurea-based compounds, such as 3-(3,4-dichlorophenyl)-1,1-dimethyl urea (common name: DCMU); and triazine-based compounds, such as 2-methylthio-4-t-butylamino-6-cyclopropylamino-5-triazine.

One type of these active ingredients may be used alone or at least two types thereof may be used in combination. In addition, the proportions at which these active ingredients are incorporated may be suitably selected corresponding to the application.

Although there are no particular limitations on the preparation form of the construction material preservative of the present invention, examples thereof include aqueous liquids such as an aqueous solution or aqueous suspension, wettable powders, and water-soluble powders.

The aforementioned aqueous liquid may be obtained directly by preparing the water-soluble silver-amino acid complex in water, as mentioned above.

In the case the preparation form of the construction material preservative of the present invention is an aqueous liquid, it may be used to treat construction materials such as wood either in its undiluted form or after suitably diluting.

Even though the construction material preservative of the present invention is aqueous, it is resistant to leaching. This is presumed to be because, when the active ingredient of the construction material preservative according to the present invention in the form of the water-soluble silver-amino acid complex is impregnated into wood, it changes to a polymer and becomes water-insoluble.

The aforementioned wettable powder or water-soluble powder is a solid preparation in the form of a powder or granules and the like, which is preferable from the viewpoints of convenience during storage and transport and long-term stability of the complex.

Specific examples of methods for formulating into a solid preparation include: a method in which the aforementioned water-soluble silver-amino acid complex is adsorbed onto a solid carrier made of clay, talc, silica, alumina, montmorillonite, or the like; a method in which the aforementioned water-soluble silver-amino acid complex is made to be coexistent with a water-soluble carrier, such as a sugar, urea, or alkaline metal salt; and a method in which the aforementioned water-soluble silver-amino acid complex is transformed into a powder by dropping into ethanol.

In the case the preparation form of the construction material preservative of the present invention is a wettable powder or water-soluble powder, it may be used to treat wood by putting into the form of an aqueous liquid by dissolving or suspending in water, or a solvent containing water, at the time of use.

There are no particular limitations on the method for treating construction materials of the present invention provided it is a method that is used to treat construction materials such as wood by using the aforementioned construction material preservative. Specific examples of treatment methods include: a method in which the aforementioned construction material preservative is coated onto a construction material by brush coating, spray coating, or the like; a method in which a construction material is immersed in the aforementioned construction material preservative; and a method in which the aforementioned construction material preservative is injected into a construction material at normal pressure, under reduced pressure or by applying pressure. The construction material treatment method can be suitably selected corresponding to the application, shape, and so forth, of the wood or other construction material. Among these, the immersion or injection method is preferable from the viewpoint of long-term storageability of the construction material, and pressurized injection is particularly preferable. The construction material preservative of the present invention demonstrates sustained long-term effects since it easily permeates into construction materials as a result of being applied using these treatment methods, while also becoming fixed within the structure of the construction material after being applied, thereby making it resistant to leaching.

The construction material preservative of the present invention may be preferably applied to the control of wood pests, wood decaying fungi and other fungi that infest wood.

Examples of wood pests include *Reticulitermes speratus* and *Coptotermes formosanus* belonging to the family Rhinotermitidae, and *Incisitermes minor* belonging to the family Kalotermitidae, in the order Isoptera. Examples of wood decaying fungi include: brown rot fungi, such as *Tyromyces palustris, Serpula lacrymans, Coniophora puteana, Gloeophyllum trabeum*, or *Gloeophyllum sepiarium*; and white rot fungi, such as *Trametes versicolor, Polyporus tuberaster*, or *Schizophyllum commune*.

Among these, the construction material preservative of the present invention is more preferably applied for the control of termites.

All types of materials to be used to construct personal residences, offices, public buildings or other arbitrary buildings or structures may be used as treatment targets of the construction material preservative of the present invention in the form of construction materials. Here, a "material to be used to construct a building or structure" refers to a material for constituting the basic form of a building or structure, and although this includes constituent materials of those sites provided with a structure that is initially incorporated in a building or structure in the manner of lighting facilities, vibration damping facilities or soundproofing facilities, it does not include mechanical equipment providing additional services such as air-conditioning, electrical wiring, water and gas lines or air-conditioning ducts and the like. Specific examples of construction materials include flooring materials, wall materials, roof materials, wood, ceiling materials, insulating materials, heat shielding materials, stairways, synthetic laminated materials, repair and surface preparation materials, foundation and base materials, railings, slopes, wrought iron fixtures, eaves, interior and exterior decorative materials, interior and exterior finishing materials, soundproofing and sound-blocking materials and designed construction materials. Specific examples of insulating materials include those composed of foamed resins such as polypropylene foam, polystyrene foam or polyurethane foam. Specific examples of wood include wood materials such as logs, boards, pillars, laminates, plywood, laminated veneer, or wooden particle board, and furniture, instruments, and the like, obtained by processing these materials.

The construction material preservative of the present invention may be particularly preferably applied to foamed resin insulating materials or wood.

The processed construction material of the present invention may be obtained by treating the aforementioned construction materials by the aforementioned construction material processing methods using the aforementioned construction material preservative. A processed construction material obtained in this manner demonstrates sustained control effects against harmful organisms over a long period of time since the aforementioned water-soluble silver-amino acid complex becomes fixed in the structure of the construction material thereby making it resistant to leaching.

EXAMPLES

The following provides a more detailed explanation of the present invention by indicating examples thereof. However, the present invention is not limited by the following examples.

Example 1

1.074 g of silver oxide (guaranteed reagent, Wako Pure Chemical Industries, Ltd.), 2.88 g of L-histidine (guaranteed reagent, Wako Pure Chemical Industries, Ltd.) and 96.046 g of water were placed in a suitable container and dissolved by stirring for 30 minutes or more at room temperature to obtain a construction material preservative composed of an aqueous solution containing a silver-histidine complex composed of 1 molar part of silver and 1 molar part of histidine (silver concentration: 1% by weight).

Example 2

1.074 g of silver oxide (guaranteed reagent, Wako Pure Chemical Industries, Ltd.), 1.65 g of L-methionine (guaranteed reagent, Wako Pure Chemical Industries, Ltd.) and 97.276 g of water were placed in a suitable container and dissolved by stirring for 60 minutes or more at 50° C. to obtain a construction material preservative composed of an aqueous solution containing a silver-methionine complex composed of 1 molar part of silver and 1 molar part of methionine (silver concentration: 1% by weight).

Test Example 1

Wood Mold Prevention Test

The construction material preservatives obtained in Example 1 and Example 2 were respectively diluted with distilled water to obtain aqueous solutions having silver concentrations of 12.5 ppm, 25 ppm, 50 ppm, 100 ppm and 200 ppm. Test pieces of Red Pine KD wood (0.5×2×2 cm) were immersed for 10 minutes in each of the aforementioned aqueous solutions, followed by allowing to air-dry overnight. Distilled water was used instead of the aforementioned aqueous solutions as a control.

2% by weight of an aqueous agar solution was poured into Petri dishes and allowed to solidify, and the aforementioned wood test pieces were placed on the agar. 100 μl aliquots of spore suspensions of each of the mold strains shown in Table 1 (spore concentration: $1 \times 10^5$/mL) were dropped onto the wood test pieces and their periphery, followed by covering the Petri dishes. The Petri dishes were then incubated for 2 weeks in an incubator at 27° C., followed by evaluation of the degree of wood infestation based on the criteria indicated below. Each test was repeated twice. The results are shown in Tables 1 and 2.

Evaluation Criteria:

−: No mold growth

±: Slight mold growth observed

+: Mold growth covering less than 25% of total surface area of wood test piece

++: Mold growth covering 25% to less than 50% of total surface area of wood test piece +++: Mold growth covering 50% or more of total surface area of wood test piece

TABLE 1

| Mold Strain | Distilled water | Silver-histidine complex aqueous solution Silver concentration (ppm) | | | | |
|---|---|---|---|---|---|---|
| | | 12.5 | 25 | 50 | 100 | 200 |
| *Aspergillus niger* | +++ | +++ | + | − | − | − |
| *Penicillium funiculosum* | +++ | − | − | − | − | − |
| *Aureobasidium pullulans* | +++ | − | − | − | − | − |
| *Gliocladium virens* | +++ | +++ | +++ | − | − | − |
| *Rhizopus oryzae* | +++ | ++ | +++ | − | − | − |
| *Alternaria alternate* | +++ | − | − | − | − | − |
| *Fusarium* sp. | +++ | − | − | − | − | − |
| *Trichoderma* sp. | +++ | ± | − | − | − | − |

TABLE 2

| Mold Strain | Distilled water | Silver-methionine complex aqueous solution Silver concentration (ppm) | | | | |
|---|---|---|---|---|---|---|
| | | 12.5 | 25 | 50 | 100 | 200 |
| *Aspergillus niger* | +++ | +++ | ++ | − | − | − |
| *Penicillium funiculosum* | +++ | − | − | − | − | − |
| *Aureobasidium pullulans* | +++ | − | − | − | − | − |
| *Gliocladium virens* | +++ | +++ | ± | − | − | − |
| *Rhizopus oryzae* | +++ | − | − | − | − | − |
| *Alternaria alternate* | +++ | − | − | − | − | − |
| *Fusariura* sp. | +++ | − | − | − | − | − |
| *Trichoderma* sp. | +++ | − | − | − | − | − |

Test Example 2

Wood Decaying Fungi Test

The construction material preservatives obtained in Example 1 and Example 2 were respectively diluted with distilled water to obtain aqueous solutions having silver concentrations of 250 ppm, 500 ppm, 1000 ppm and 2000 ppm. Test pieces of Red Pine KD wood (0.5×2×2 cm) were immersed for 10 minutes in each of the aforementioned aqueous solutions, followed by allowing to air-dry overnight for use as a test group.

In addition, the aforementioned Red Pine KD wood test pieces were immersed for 10 minutes in distilled water, followed by allowing to air-dry overnight for use as a control group.

Potato dextrose agar medium (Eiken Chemical Co., Ltd.) containing 1% by weight of red pine sawdust was poured into Petri dishes and allowed to solidify, the aforementioned wood test pieces were placed thereon, and mycelia of test organisms removed with a cork borer were respectively placed thereon, followed by covering the Petri dishes. The Petri dishes were incubated for 4 weeks by placing in an incubator at 27° C. Subsequently, the degree of mycelia coverage on the wood test pieces was evaluated according to the method indicated below. Each test was repeated three times. The results are shown in Tables 3 and 4.

<Evaluation Method>

The wood test pieces were first evaluated based on the infestation indices indicated below.

0: No mycelia covering test piece 0.5: Mycelia slightly covering test piece

1: Mycelia covering about ¼ the total surface area of the test piece

2: Mycelia covering about ½ the total surface area of the test piece

3: Mycelia covering about ¾ the total surface area of the test piece

4: Mycelia covering the entire surface of the test piece

Next, the resulting indices were substituted into the following equation to determine the degree of infestation.

Degree of infestation=Σ(infestation index of test piece)/(4×(3 repetitions))×100

Moreover, control values were determined according to the following equation from the resulting degree of infestation.

Control value=(degree of infestation of control group−degree of infestation of test group)/(degree of infestation of control group)×100

Final evaluations were made by evaluating the resulting control value based on the criteria indicated below.

−: 80% or more and less than 100%

±: 60% or more and less than 80%

+: 40% or more and less than 60%

++: 20% or more and less than 40%

+++: 0% or more and less than 20%

TABLE 3

| Wood decaying fungi | Silver-histidine complex aqueous solution Silver concentration (ppm) | | | |
|---|---|---|---|---|
| | 250 | 500 | 1000 | 2000 |
| *Trametes versicolor* | ++ | ++ | + | − |
| *Coriorus hirsutus* | +++ | +++ | +++ | ± |

TABLE 4

| Wood decaying fungi | Silver-methionine complex aqueous solution Silver concentration (ppm) | | | |
|---|---|---|---|---|
| | 250 | 500 | 1000 | 2000 |
| Trametes versicolor | ± | − | − | − |
| Coriorus hirsutus | + | ± | − | − |
| Polyporus sp. | ± | + | − | − |

Test Example 3

Termite Prevention Test

The silver-histidine complex aqueous solution obtained in Example 1 was diluted with distilled water to obtain an aqueous solution having a silver concentration of 200 ppm. A test piece of Red Pine KD wood (0.5×4×4 cm) was immersed in the aforementioned aqueous solution for 20 minutes followed by allowing to air-dry overnight. Distilled water was used instead of the aforementioned aqueous solution as a control.

An acrylic cylinder measuring 8 cm in diameter and 6 cm in height was placed vertically on a horizontal stand, and anhydrite was spread onto the bottom end of the cylinder to a thickness of about 5 mm and allowed to harden to form a bottomed cylinder having anhydrite for the bottom thereof. The aforementioned wood test piece was placed on the anhydrite bottom plate and *Coptotermes formosanus* (consisting of 30 worker termites and 3 soldier termites) were placed in the bottomed cylinder.

Absorbent cotton impregnated with water was placed in a glass Petri dish, the aforementioned bottomed cylinder was placed on the absorbent cotton, and the termites were allowed to proliferate for 12 days in a dark location at 28° C. The percentage of the 30 worker termites that died or were near death was calculated over time. In addition, the damage to the wood test piece after 12 weeks had elapsed since the termites were released was observed visually to assess for the presence or absence of feeding damage. The results are shown in Table 5.

TABLE 5

| | Percentage dead or near death (%) | | | Damage |
|---|---|---|---|---|
| Chemical Agent | After 5 days | After 7 days | After 12 days | After 12 days |
| Silver-histidine complex aqueous solution | 16.7 | 53.3 | 70.0 | Absence of feeding damage |
| Distilled water | 3.3 | 10.0 | 13.3 | Presence of Feeding damage |

On the basis of the above results, the construction material preservative containing a silver-amino acid complex and water of the present invention was determined to demonstrate control effects against molds, wood decaying fungi and termites that damage wood.

Test Example 4

Termite Prevention Test

Ion exchange water was added to an aqueous solution containing a water-soluble silver-histidine complex composed of 1 molar part of silver and 2 molar parts of histidine as a water-soluble silver-amino acid complex and a bulk acetamiprid (manufactured by Nippon Soda Co., Ltd.) as an insecticide component, followed by dissolving and mixing to produce compositions containing each components at the concentrations shown in Table 6 (Examples 3 to 7 and Comparative Examples 1 to 3).

Two sheets of filter paper having a diameter of 55 mm were placed in the bottom of plastic cup having a volume of 90 ml, and 1 ml of each of the compositions shown in Table 1 was dropped onto the center thereof and allowed to air-dry. 10 worker *Coptotermes formosanus* and 1 soldier *Coptotermes formosanus* termite were released onto the filter paper and a cover having ventilation holes was put thereon. The presence or absence of termites among the 10 worker termites that died or were near death at 5 and 7 days after being released was evaluated, and the degree of filter paper feeding damage from the time the termites were released to 7 days after their release was observed. The results are shown in Table 1.

Degree of Feeding Damage:
+: Prominent feeding damage
±: Slight feeding damage
−: No feeding damage

TABLE 6

| Test Group | Acetamiprid concentration (ppm) | Silver-histidine complex concentration (ppm) | Percentage of dead or near death (%) | | Degree of feeding damage |
|---|---|---|---|---|---|
| | | | After 5 days | After 7 days | |
| Example 3 | 6.25 | 0.039 | 60 | 90 | − |
| Example 4 | 6.25 | 0.39 | 60 | 90 | − |
| Example 5 | 3.125 | 0.39 | 20 | 30 | − |
| Comp. Ex. 1 | 6.25 | 0 | 30 | 50 | ± |
| Comp. Ex. 2 | 3.125 | 0 | 0 | 0 | + |
| Example 6 | 0 | 0.039 | 0 | 0 | + |
| Example 7 | 0 | 0.39 | 0 | 0 | ± |
| Comp. Ex. 3 | 0 | 0 | 0 | 0 | + |

On the basis of the results of Table 6, the construction material preservative of the present invention was determined to demonstrate extremely high control effects against termites and the retention of those control effects was sufficiently long.

Test Example 5

Termite Prevention Test

Ion exchange water was added to an aqueous solution containing a water-soluble silver-histidine complex composed of 1 molar part of silver and 2 molar parts of histidine as a water-soluble silver-amino acid complex and a bulk acetamiprid (manufactured by Nippon Soda Co., Ltd.) as an insecticide component, followed by dissolving and mixing to produce an aqueous solution containing 0.02% by weight (200 ppm) of acetamiprid and 0.001% by weight (10 ppm) of water-soluble silver-histidine complex for use as Example 8.

Copper salt (0.29% by weight as copper) and 0.32% by weight of quaternary ammonium salt were dissolved in ion exchange water to prepare an aqueous alkaline copper quaternary (ACQ) preservative solution for use as Comparative Example 4.

Test pieces made of polystyrene foam insulating material (2.9×2.9×2.9 cm) were immersed in respective aqueous solutions of Example 6 and Comparative Example 6 for 20 minutes, followed by allowing to air-dry overnight.

An acrylic cylinder measuring 8 cm in diameter and 6 cm in height was placed vertically on a horizontal stand, and anhydrite was spread onto the bottom end of the cylinder to a thickness of about 5 mm and allowed to harden to form a bottomed cylinder having anhydrite for the bottom thereof. One each of the aforementioned test pieces was placed on the anhydrite bottom plate and *Coptotermes formosanus* (consisting of 20 worker termites and 2 soldier termites) were placed in the bottomed cylinder.

Absorbent cotton impregnated with water was placed in a glass Petri dish, the aforementioned bottomed cylinder was placed on the absorbent cotton, and the termites were allowed to proliferate for 8 days in a dark location at 28° C. The percentage of the 20 worker termites that died or were near death was calculated over time. In addition, the damage to the test pieces after 8 days had elapsed since the termites were released was observed visually to assess for the presence or absence of feeding damage. The results are shown in Table 7.

Degree Of Feeding Damage:
+: Presence of prominent feeding damage
−: Absence of feeding damage

TABLE 7

| Chemical Agent | Percentage of dead or near death (%) | | | | Degree of feeding damage |
|---|---|---|---|---|---|
| | After 1 day | After 2 days | After 7 days | After 8 days | |
| Example 8 | 85 | 90 | 100 | 100 | − |
| Comp. Ex. 4 | 0 | 0 | 60 | 70 | + |

Based on the results of Table 7, the construction material preservative of the present invention was determined to demonstrate extremely high control effects against termites particularly in foamed resin insulating materials.

INDUSTRIAL APPLICABILITY

The construction material preservative of the present invention is extremely safe and has control effects against a wide spectrum of harmful microorganisms, including wood decaying fungi for which there are few effective chemical agents. Moreover, since it also demonstrates insecticidal effects against termites and other wood pests, it demonstrates adequate wood preservative effects without having to use in combination with other types of bactericidal agents, antibacterial agents, fungicides, insecticides, pest repellents, or the like.

The construction material preservative of the present invention has low toxicity with respect to acute oral toxicity, skin irritation or mucosal membrane irritation, and does not affect the quality of wood. Moreover, it is able to continuously demonstrate antibacterial, bactericidal, fungicidal and insecticidal effects over a long period of time. Thus, the quality of wood products treated with the construction material preservative of the present invention is not impaired over a long period of time.

In addition, in the case of combining with an insecticide component, adequate efficacy is able to be demonstrated even at a low concentration of the insecticide component due to the synergistic effects thereof.

The invention claimed is:

1. A construction material preservative comprising a water-soluble silver-histidine complex and an insecticide component, wherein
   the insecticide component is acetamiprid;
   the water-soluble silver-histidine complex consists of 1 molar part of silver and 1 to 3 molar parts of histidine; and
   0.1 parts by weight to 40 parts by weight of the insecticide component is comprised relative to 1 part by weight of the water-soluble silver-histidine complex.

2. The construction material preservative according to claim 1, further comprising water.

3. The construction material preservative according claim 1, wherein 0.0001% by weight to 0.5% by weight of the water-soluble silver-histidine complex, 0.0001% by weight to 0.5% by weight of the insecticide component, and 10% by weight or more of water are comprised.

4. A construction material processing method, comprising treating a construction material with the construction material preservative of claim 1.

5. The construction material processing method according to claim 4, wherein the treatment is at least one type selected from the group consisting of coating treatment, immersion treatment, injection treatment, and pressurized injection treatment.

6. A processed construction material obtained by the construction material processing method of claim 4.

7. The processed construction material according to claim 6, wherein the processed construction material is a foamed resin insulating material or a wood.

8. A composition comprising a water-soluble silver-histidine complex and an insecticide component, wherein
   the insecticide component is acetamiprid;
   the water-soluble silver-histidine complex consists of 1 molar part of silver and 1 to 3 molar parts of histidine; and
   0.1 parts by weight to 40 parts by weight of the insecticide component is comprised relative to 1 part by weight of the water-soluble silver-histidine complex.

* * * * *